US012617971B2

(12) United States Patent
Seo et al.

(10) Patent No.: US 12,617,971 B2
(45) Date of Patent: May 5, 2026

(54) ANTI-VIRAL COATING COMPOSITION, AND METHOD FOR FIXING ANTI-VIRAL FUSION PROTEIN TO SURFACES

(71) Applicant: AMOLIFESCIENCE CO., LTD., Seoul (KR)

(72) Inventors: In Yong Seo, Seoul (KR); Dong Sik Seo, Seoul (KR); Seon Ho Jang, Seoul (KR)

(73) Assignee: AMOLIFESCIENCE CO., LTD., Seoul (KR)

( * ) Notice: Subject to any disclaimer, the term of this patent is extended or adjusted under 35 U.S.C. 154(b) by 741 days.

(21) Appl. No.: 17/999,250

(22) PCT Filed: May 20, 2021

(86) PCT No.: PCT/KR2021/006294
§ 371 (c)(1),
(2) Date: Jan. 11, 2023

(87) PCT Pub. No.: WO2021/235873
PCT Pub. Date: Nov. 25, 2021

(65) Prior Publication Data
US 2023/0227694 A1 Jul. 20, 2023

(30) Foreign Application Priority Data

May 20, 2020 (KR) ........................ 10-2020-0060232
May 20, 2020 (KR) ........................ 10-2020-0060233
May 20, 2020 (KR) ........................ 10-2020-0060234

(51) Int. Cl.
*A61L 9/16* (2006.01)
*C07K 7/06* (2006.01)
(Continued)

(52) U.S. Cl.
CPC .............. *C09D 189/00* (2013.01); *C07K 7/06* (2013.01); *C07K 7/08* (2013.01); *C09D 7/20* (2018.01);
(Continued)

(58) Field of Classification Search
CPC ....................................................... A61L 9/16
See application file for complete search history.

(56) References Cited

U.S. PATENT DOCUMENTS

2012/0171354 A1* 7/2012 O'Neill ................... A61L 27/34
427/2.24
2013/0052712 A1 2/2013 Cha et al.
(Continued)

FOREIGN PATENT DOCUMENTS

KR 20120047363 A 5/2012
KR 20130021951 A 3/2013
(Continued)

OTHER PUBLICATIONS

English Machine Translation of Lee et al. WO2017026759 (Year: 2017).*
(Continued)

*Primary Examiner* — Donald R Spamer
(74) *Attorney, Agent, or Firm* — ROTHWELL, FIGG, ERNST & MANBECK, P.C.

(57) ABSTRACT

An antiviral coating composition is provided. An antiviral coating composition according to one embodiment of the present invention is implemented by including an antiviral component comprising an antiviral fusion protein in which an antiviral motif is bound to an adhesive protein. According to the present invention, the composition has excellent processability enabling easy provision on various surfaces of various products, has adhesion sustainability enabling an adhesive state to be maintained for a long period of time (Continued)

after being adhered to a surface, and has activity sustainability enabling antiviral activity to be maintained for a long period of time without a loss in activity according to external conditions during preparation, storage and use.

10 Claims, 3 Drawing Sheets

Specification includes a Sequence Listing.

(51) Int. Cl.

| | | |
|---|---|---|
| *C07K 7/08* | (2006.01) | |
| *C09D 7/20* | (2018.01) | |
| *C09D 189/00* | (2006.01) | |
| *C09J 189/00* | (2006.01) | |

(52) U.S. Cl.
CPC ......... *C09J 189/00* (2013.01); *C07K 2319/00* (2013.01)

(56) References Cited

U.S. PATENT DOCUMENTS

| | | | |
|---|---|---|---|
| 2013/0205416 | A1 | 8/2013 | Nash et al. |
| 2016/0017279 | A1 | 1/2016 | Cha et al. |
| 2018/0311599 | A1* | 11/2018 | Zhong .................... B01J 20/261 |
| 2019/0008828 | A1* | 1/2019 | Sun ......................... A61K 45/06 |
| 2019/0203178 | A1 | 7/2019 | Seo et al. |

FOREIGN PATENT DOCUMENTS

| | | | |
|---|---|---|---|
| KR | 20160144073 A | | 12/2016 |
| KR | 20170132994 A | | 12/2017 |
| WO | WO2017026759 | * | 2/2017 |

OTHER PUBLICATIONS

Thermo Fisher "Carbodiimide Crosslinker Chemistry". Wayback Machine Capture Apr. 1, 2020 (Year: 2020).*

Ying et al. (Identification of a New Region of SARS CoV S Protein Critical for Viral Entry), J. Mol. Biol. (2009) 394, 600-605 (Year: 2009).*

Hutsell et al., "High-Affinity Immobilization of Proteins Using Biotin- and GST-Based Coupling Strategies", Methods in Molecular Biology, 2010, vol. 627, pp. 75-90.

International Search Report issued in PCT/KR2021/006294, dated Sep. 1, 2021, 7 pgs.

* cited by examiner

[Figure]

ANTI-VIRAL COATING COMPOSITION, AND METHOD FOR FIXING ANTI-VIRAL FUSION PROTEIN TO SURFACES

CROSS-REFERENCE TO RELATED APPLICATIONS

This application is a 35 U.S.C. 371 National Phase Entry Application from PCT/KR2021/006294 filed May 20, 2021, which claims priority to and the benefit of Korean Patent Application Nos. 10-2020-0060232, 10-2020-0060233 and 10-2020-0060234, all filed on May 20, 2020, the disclosures of which are incorporated herein by reference in their entirety.

The instant application contains a Sequence Listing which has been submitted via EFS-Web and is hereby incorporated by reference in its entirety. Said Sequence Listing, created on Nov. 18, 2022, is named SOP116078US.ST25.TXT and is 13000 bytes in size.

TECHNICAL FIELD

The present invention relates to a coating composition, and more particularly, to a coating composition having antiviral activity and a method for immobilizing an antiviral fusion protein on surfaces.

BACKGROUND

SARS, which began to spread in early 2003, MERS, which began infecting people in 2012 and also caused 186 cases in South Korea in 2015, and COVID-19 that began in late 2019 and has spread all over the world to date are all caused by viruses, and the need for a sanitary and safe living environment has significantly increased against this background. In particular, considering that it takes a considerable amount of time to develop a vaccine after the outbreak of diseases caused by viruses, the demand for various antiviral products to create a safe living environment is further increasing.

All of the above-described diseases are caused by coronaviruses, and ethanol, sodium hypochlorite, an iodophor, peracetic acid, formaldehyde, glutaraldehyde, and ethylene oxide gas are reported to be effective as disinfectants against coronaviruses. Further, 1-adamantanamine hydrochloride, thiosemicarbazide, an arabinosyl nucleoside, nucleoside, 2,3-dideoxynucleoside, pyrophosphate derivatives and the like are known as antiviral agents. However, since the activity of these antiviral components is temporary or the activity may be easily lost due to various external factors such as temperature and humidity, the antiviral effect and durability of antiviral products cannot be expected.

In addition, even when there is an antiviral effect by itself, antiviral activity is lost during the process of applying the components to products or there is also a problem in that a process of providing products with antiviral components is not easy.

Furthermore, even when a product is provided with an antiviral component while maintaining antiviral activity, there are a durability problem such as easy detachment from the product and a storage stability problem such as loss of activity during storage at room temperature.

SUMMARY OF THE INVENTION

The present invention has been devised in consideration of the above points, and an object of the present invention is to provide an antiviral coating composition having excellent processability enabling easy provision on various surfaces of various products, having adhesion sustainability enabling an adhesive state to be maintained for a long period of time after being adhered to a surface, and having activity sustainability enabling antiviral activity to be maintained for a long period of time without a loss in activity according to external conditions during preparation, storage and use, and a method for immobilizing an antiviral fusion protein on surfaces.

To solve the above-described problems, the present invention provides an antiviral coating composition including an antiviral component including an antiviral fusion protein in which an antiviral motif is bound to an adhesive protein.

According to one embodiment of the present invention, the antiviral motif may be bound to the C-terminus or N-terminus of the adhesive protein.

Further, the antiviral motif may target a protein that binds to a host cell receptor to disable or disrupt the protein, or may perform the function of disrupting the viral membrane.

In addition, the antiviral motif may include any one peptide selected from the group consisting of amino acid sequences of SEQ ID NOS: 1 to 8 or a peptide in which one or more amino acid sequences selected from the above group are linked, or may consist of them.

Furthermore, the adhesive protein may be a mussel-derived adhesive protein.

Further, the adhesive protein may include any one protein selected from the group consisting of amino acid sequences of SEQ ID NOS: 9 to 22 or a protein in which one or more amino acid sequences selected from the above group are linked, or may consist of them.

In addition, the adhesive protein may contain a DOPA residue. In this case, the DOPA residue may be a DOPA residue into which some or all tyrosine residues of the adhesive protein are modified through an enzyme.

Furthermore, an aggregation-inducing component including a carbodiimide-based coupling agent and a hydroxy succinimide-based reactive agent may be further included.

Further, an active component activating the aggregation-inducing component may be further included, and the active component may include sodium acetate.

In addition, the carbodiimide-based coupling agent and the succinimide-based reactive agent may be included at a weight ratio of 1:0.5 to 20 in the aggregation-inducing component, and the carbodiimide-based coupling agent may be mixed in an amount of 50 to 200 parts by weight with respect to 100 parts by weight of the antiviral fusion protein.

Furthermore, a solvent that is water or ethanol may be further included.

Further, an aggregation-inducing component including a carbodiimide-based coupling agent and a hydroxy succinimide-based reactive agent is further included, and the antiviral coating composition may be a two liquid-type coating composition including a first solution including an antiviral component and a second solution including the aggregation-inducing component.

In addition, the first solution may further include water as a solvent, and the second solution may further include ethanol as a solvent.

Furthermore, the present invention provides a method for immobilizing an antiviral component on surfaces, the method including treating the surface of a target with the antiviral coating composition according to the present invention and drying the antiviral coating composition.

According to one embodiment of the present invention, the treatment may be performed by electrospraying or impregnating the antiviral coating composition onto the target surface.

Further, the target surface may be treated with the anti-viral coating composition through electrospraying, the anti-viral coating composition further includes an aggregation-inducing component including a carbodiimide-based coupling agent and a hydroxy succinimide-based reactive agent, and is prepared by separating into a first solution including an antiviral component and water and a second solution including the aggregation-inducing component and ethanol, and the first solution and the second solution are mixed in an electrospraying device, and then the target surface may be treated with the resulting mixture through electrospraying.

In addition, the temperature of the second solution may be 0 to 15° C.

Furthermore, modifying a tyrosine residue possessed by an adhesive protein in an antiviral fusion protein into a DOPA residue before the surface of a target is treated with the antiviral coating composition may be further included.

Further, the modification may be performed by including (1) preparing a solution in which an antiviral fusion protein is dissolved in a buffer solution containing ascorbic acid at a concentration of 25 to 100 mM such that the concentration is 0.1 to 10 mg/ml, (2) preparing the solution in an oxygen-saturated state, and then modifying a tyrosine residue in an adhesive protein into a DOPA residue by mixing tyrosinase with the solution and (3) performing desalting with acetic acid.

In addition, the present invention provides an article including a surface and an antiviral coating layer formed by treating the surface with the antiviral coating composition according to the present invention.

According to one embodiment of the present invention, the surface is non-porous, and the antiviral coating layer may be formed by aggregating particles formed of an antiviral fusion protein.

The antiviral coating composition according to the present invention has excellent processability enabling easy provision on various surfaces such as flat or curved surfaces, smooth or rough surfaces, or porous surfaces of various products. Furthermore, the antiviral coating composition according to the present invention can be applied to various products ranging from air filters, water treatment filters such as drinking water filters, various sanitary products such as masks, and general fibers such as underwear and socks to special fibers for medical use as the antiviral coating composition according to provide adhesion sustainability enabling an adhesive state to be maintained for a long period of time after being adhered to a surface, and has activity sustainability enabling antiviral activity to be maintained for a long period of time without a loss in activity according to external conditions during preparation, storage and use.

DETAILED DESCRIPTION

Hereinafter, embodiments of the present invention will be described in detail with reference to the accompanying drawings such that a person with ordinary skill in the art to which the present invention pertains can easily carry out the present invention. The present invention can be embodied in various forms, and is not limited to the embodiments described herein.

An antiviral coating composition according to one embodiment of the present invention includes an antiviral component including an antiviral fusion protein in which an antiviral motif is bound to an adhesive protein.

The antiviral component includes an antiviral fusion protein, and the antiviral fusion protein is formed by allowing an antiviral motif to bind to an adhesive protein.

The antiviral motif may be a motif that functions to suppress viral proliferation, destroy the virus itself, or block infection by participating in a mechanism by which a host is infected by the virus.

Figure 1:
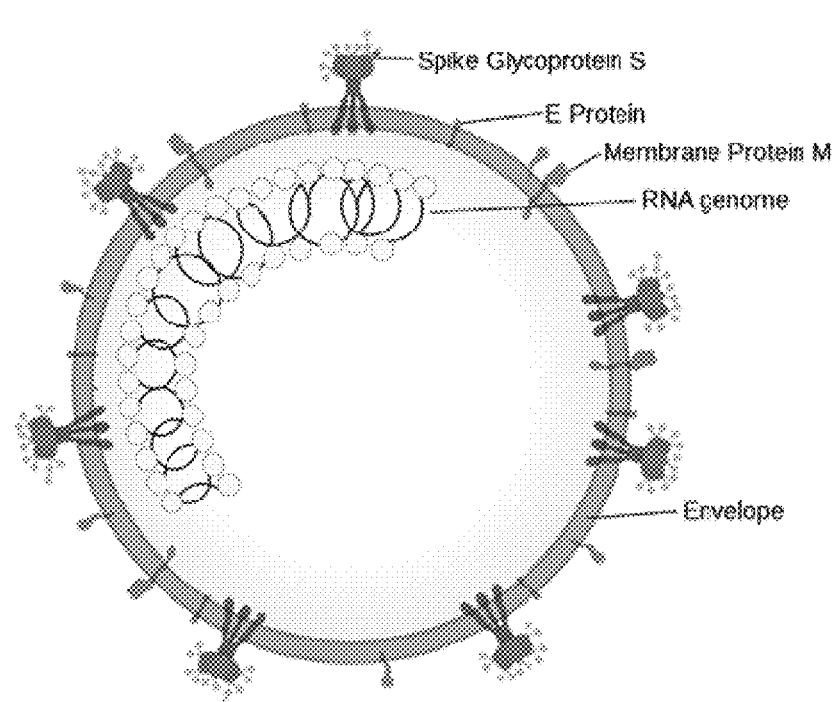
FIG. 1 is a cross-sectional schematic view of a corona-virus.
Figure 2:
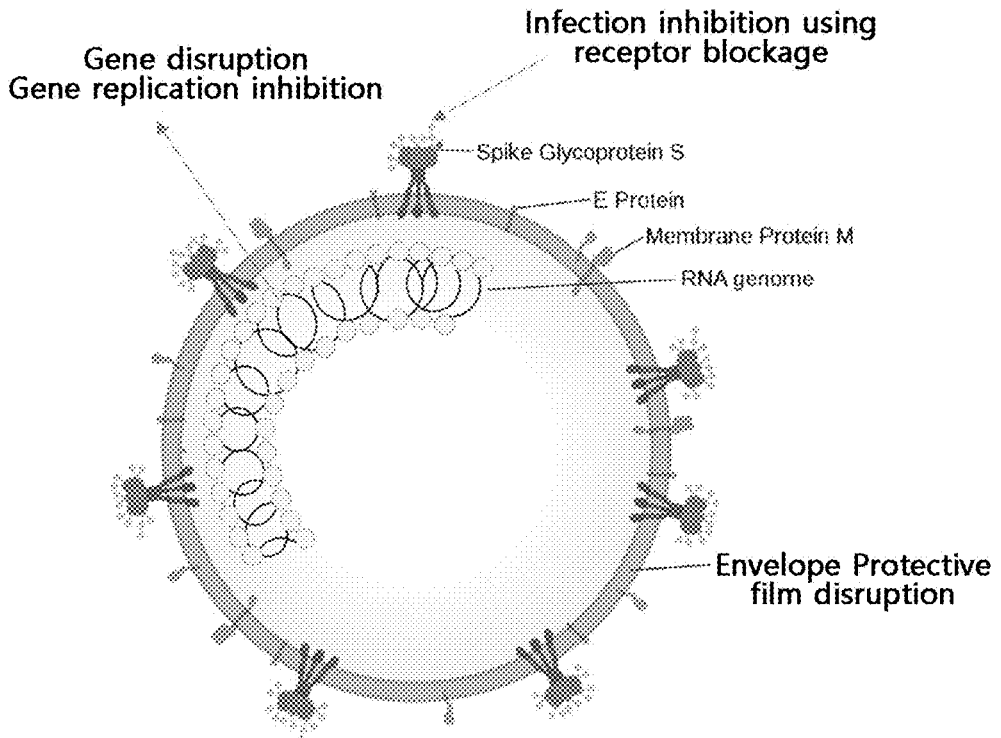
FIG. 2 is a schematic view related to targets by which antiviral motifs can act against coronaviruses.

For example, referring to FIG. 1, the antiviral motif may have a function of directly or indirectly disrupting the outer membrane, which is the protective film of the virus. Alternatively, when a virus infects a host cell, the antiviral motif may have a function of directly or indirectly disrupting a protein (for example, a spike protein of a coronavirus) bound to the host cell, or directly or indirectly disabling the protein. Here, the direct or indirect means that the antiviral motif directly performs the corresponding function or participates in the initial or intermediate process in ultimately performing the corresponding function.

The antiviral motif can be used without limitation as long as the antiviral motif is a known motif that is known to have an antiviral effect such as destruction or inactivation of the above-described virus. For example, the antiviral motif may be any one peptide selected from the group consisting of amino acid sequences of SEQ ID NOS: 1 to 8, a peptide in which one or more amino acid sequences selected from the above group are linked, or a peptide including one or more amino acid sequences selected from the above group as a basic sequence. For example, the motifs according to SEQ ID NOS: 1 and 2 may be useful for SARS coronaviruses, the motifs according to SEQ ID NOS: 3 to 8 may be useful for influenza A viruses, and in addition, the motif according to SEQ ID NO: 7 may also be useful for HSV.

Further, the antiviral motif may be, for example, a peptide with 3 to 100 amino acids, more preferably 3 to 20 amino acids.

In addition, the virus which the antiviral motif targets is not limited as long as the virus is a known virus, and non-limiting examples thereof include JV, HSV, HIV, IPNV, VHSV, SHRV, HCMV, IAV, Japanese encephalitis virus, Ebola virus, rhinovirus, adenovirus, measles virus, hepatitis B virus, influenza A, and the like.

The above-described antiviral motif itself may be included in the coating composition to treat the surface of a substrate, but it is not easy to immobilize the antiviral motif alone on the surface of the substrate for a long time. Accordingly, the present invention is implemented in the form of a fusion protein in which the antiviral motif is bound to a conjugated protein. The adhesive proteins may function as an adhesive component that provides adhesion between the antiviral motif and the substrate surface. Meanwhile, when protein is used as an adhesive component, there is an advantage in that the coating composition can be used even for uses that directly may affect the human body because the protein is non-toxic compared to a polymer-based adhesive component.

Furthermore, the bond between the antiviral motif and the adhesive protein may be a covalent bond, and more specifically, the antiviral motif may be bound to the carboxy terminus, the amino terminus, or both the carboxy terminus and the amino terminus of the adhesive protein by a peptide bond. Meanwhile, the antiviral motif and the adhesive protein may be bound by a known method, and for example, may be prepared by a recombinant protein production method using *Escherichia coli*. Meanwhile, the adhesive protein and the antiviral motif may be directly bound by a covalent bond, but the bond is not limited thereto, and it should be noted that the adhesive protein and the antiviral motif may be indirectly bound by a covalent bond, and the like by adding a third material as a spacer.

Further, the adhesive protein can be used without limitation as long as the adhesive protein is a protein having a known adhesion function, but may be a mussel-derived adhesive protein, and a known adhesive protein commonly called a mussel-derived adhesive protein can be used without limitation. Preferably, the adhesive protein may include any one protein selected from the group consisting of amino acid sequences of SEQ ID NOS: 9 to 22 or a protein in which one or more amino acid sequences selected from the above group are linked.

In addition, the antiviral component may further include a heterologous material having antiviral functions in addition to the above-described antiviral fusion protein. The heterologous material may be a known organic material or inorganic material. For example, the heterologous material may be an inorganic material with a substituent having proton-donating or proton-accepting properties disposed on the surface with which the virus is brought into contact, and specific examples thereof include phosphate compounds of titanium group elements such as zirconium phosphate, hafnium phosphate, and titanium phosphate and inorganic phosphate compounds such as aluminum phosphate and hydroxyapatite (phosphate minerals); inorganic silicate compounds such as magnesium silicate, silica gel, aluminosilicate, sepiolite (hydrous magnesium silicate), montmorillonite (silicate mineral), and zeolite (aluminosilicate); alumina, titania, hydrous titanium oxide, and the like. Alternatively, the heterologous material may be a metal such as silver or a salt containing ions thereof.

Furthermore, the antiviral coating composition according to one embodiment of the present invention may further include a solvent which dissolves the above-described antiviral fusion protein or a buffer solution which stabilizes the above-described antiviral fusion protein. The solvent may be water and/or an organic solvent, and 20 to 100 mM Tris or a sodium bicarbonate buffer solution with a pH of 8 to 8.5 may be used.

Further, the above-described antiviral fusion protein may be contained at a concentration of 0.001 to 1 mg/ml, and as another example, 0.001 to 0.2 mg/ml in the antiviral coating composition, and when the above-described antiviral fusion protein is contained at a high concentration, antiviral properties may be improved, but when the surface to which the coating composition is applied is porous, there is a concern that the resulting coating layer may clog pores on the surface.

Meanwhile, among antiviral fusion proteins, an adhesive protein, particularly, a mussel-derived adhesive protein is known to have adhesion properties itself, but as a result of studies by the present inventors, when these adhesive proteins are used as they are, they may exhibit no or insignificant levels of adhesion (or cohesion) properties, making it difficult to immobilize the antiviral motif on the substrate surface. Accordingly, the antiviral fusion protein in the antiviral coating composition, particularly, the adhesive protein among the antiviral fusion proteins may contain a DOPA residue in order to exhibit more improved adhesion properties with the substrate surface. Alternatively, the antiviral coating composition may further contain an aggregation-inducing component including a carbodiimide-based coupling agent and a hydroxy succinimide-based reactive agent.

First, an antiviral coating composition in which the adhesive protein contains a DOPA residue in the antiviral fusion protein will be described.

As described above, in the case of an adhesive protein, particularly, a mussel-derived adhesive protein by itself, it is difficult for the adhesive protein itself to exhibit sufficient adhesive and cohesive properties. However, when a DOPA residue is contained, there is an advantage in that the antiviral motif can be easily and strongly immobilized on the surface of the target through the DOPA residue. The DOPA residue may be provided in an antiviral fusion protein through modification, the modification modifies some or all of the tyrosine residues contained within the adhesive protein into DOPA residues, and such modification may be performed appropriately using known methods. For example, the modification may be performed using an enzyme, and the enzyme may be, for example, tyrosinase.

Specifically, the modification may be performed by including (1) preparing a solution in which an antiviral fusion protein is dissolved in a buffer solution containing ascorbic acid, (2) preparing the solution in an oxygen-saturated state, and then modifying a tyrosine residue in an adhesive protein into a DOPA residue by mixing tyrosinase with the solution and (3) performing desalting with acetic acid.

In this case, in Step (1), the buffer solution contains ascorbic acid as an antioxidant at a concentration of 25 to 100 mM, an antiviral fusion protein may be provided at a final concentration of 0.1 to 10 mg/ml in the solution, and the buffer solution may include 20 to 100 mM sodium acetate and 20 to 100 mM sodium borate.

In addition, Step (2) may be performed by saturating the prepared solution with oxygen in the solution while injecting oxygen for 10 minutes to 1 hour, adding tyrosinase to a final concentration of 10 to 50 μg/ml, mixing and stirring the resulting mixture under oxygen conditions for 30 minutes to 2 hours, and then terminating the reaction by adding acetic acid to a final concentration of 2 to 10%.

Furthermore, Step (3) may be performed by desalting and concentrating the reaction solution in which the reaction is terminated with a 1 to 10% acetic acid solution.

Further, after the modification is performed up to Step (3), the antiviral fusion protein modified to contain a DOPA residue may be prepared in a powder form by lyophilization.

An antiviral fusion protein containing a DOPA residue prepared by the above-described method may be easily immobilized on the desired substrate surface without additional adhesive components, and as other adhesive components are not used, there is an advantage in that it is possible to prevent the deterioration or inactivation of activity due to unintended chemical reactions between other components and antiviral motifs and physical blocking.

However, as the improvement of the adhesion of the antiviral fusion protein by modification into the above-described DOPA residue requires additional cost, time, and effort, the coating composition according to one embodiment of the present invention may further include an aggregation-inducing component including a carbodiimide-based coupling agent and a hydroxy succinimide-based reactive agent. The aggregation-inducing component is a material that introduces an antiviral fusion protein to the surface of a target to be treated, and may improve adhesion between the coating layer of the antiviral fusion protein and the surface of the target compared to the case where the surface of the target is treated with the antiviral fusion protein alone using a typical method. Specifically, the aggregation-inducing component aggregates the antiviral fusion protein into particles, and an antiviral coating layer may be implemented in such a manner that these particles are adsorbed on the surface of the substrate to form aggregates. An antiviral coating composition including an aggregation-inducing component may immobilize an antiviral motif on the surface of a target with improved adhesive strength, may also sustain antiviral performance by preventing or minimizing degradation, denaturation, and the like of the antiviral motif at room temperature for a long period of time, and may improve storage stability.

Meanwhile, it is difficult to see that the granular form in which the antiviral fusion protein is aggregated by the aggregation-inducing component is due to a specific chemical bond between the fusion proteins, for example, an amino bond between a carboxyl group and an amine group by a carbodiimide-based coupling agent known in the art, which is because a plurality of hydroxy groups included in an adhesive protein, for example, a mussel-derived adhesive protein may also react with a carbodiimide-based coupling agent. Therefore, it is difficult to see that the granular form formed by the antiviral fusion protein having a plurality of reaction sites according to the present invention is due to a specific reaction and the resulting chemical bond, and it may be seen as a unique result occurring according to the combination between antiviral fusion proteins containing an aggregation-inducing component and an adhesive protein.

The carbodiimide-based coupling agent can be used without limitation in the case of a coupling agent that allows antiviral fusion proteins to bind to each other, and may be, for example, 1-[3-(dimethylamino)propyl]-3-ethylcarboimide hydrochloride (EDC) or N,N'-dicyclohexylcarbodiimide (DCC).

Furthermore, the hydroxy succinimide-based reactive agent is provided to increase the efficiency with which antiviral fusion proteins are aggregated with each other by preventing the antiviral fusion protein coupled with carbodiimide from being hydrated, and may be, for example, one of N-hydroxysuccinimide (NHS) and N-hydroxysulfosuccinimide (Sulfo-NHS) or a mixture thereof.

The aggregation-inducing component may include the carbodiimide-based coupling agent and the hydroxy succinimide-based reactive agent at a weight ratio of 1:0.5 to 20, more preferably 1:0.5 to 10, and even more preferably 1:0.5 to 3. When they are not included at an appropriate ratio, it is difficult to achieve the intended effect of the present invention, and there is a concern that when the durability and storage periods of the implemented antiviral coating layer are extended, the activity of the antiviral motif deteriorates.

Further, the aggregation-inducing component may further include sodium acetate, a phosphate buffer solution, or an MES buffer solution as an active component to improve reactivity. In this case, the active component may be included in an amount of 20 to 50 parts by weight with respect to 100 parts by weight of the total weight of the carbodiimide-based coupling agent and the hydroxy succinimide-based reactive agent, and this may be more advantageous in achieving the object of the present invention.

Meanwhile, the above-described aggregation-inducing component may be added to the coating composition as a liquid phase dissolved in a solvent, and in this case, water or an organic solvent may be used as the solvent, and preferably, water may be used, and ethanol may be further included as a solvent in terms of increasing the volatilization rate of the solvent in the coating composition. When the evaporation of the solvent is delayed after the treatment of the coating composition, the antiviral coating composition may flow from a substrate, so that it may be difficult to form an antiviral coating layer with desired content and thickness.

Meanwhile, when the antiviral coating composition further includes an aggregation-inducing component, the reaction between the antiviral fusion protein and the aggregation-inducing component may continue to occur in an antiviral coating composition state before treatment of the surface of the target with the composition due to the aggregation-inducing component, and when the target surface is treated with the antiviral coating composition after the above reaction has excessively progressed beyond the target level, it is difficult to form an antiviral coating layer, or even though the antiviral coating layer is formed, adhesive strength is weak, or the antiviral coating layer is formed to have a rough coating surface, or it is not easy to coat the antiviral coating composition such as a portion which is not coated is present, and the quality of a prepared antiviral coating layer may be poor. In addition, it may be difficult for the antiviral motif in the antiviral coating layer to be exposed to the outside, so that there is a concern that antiviral characteristics deteriorate.

Accordingly, it is preferred that the antiviral coating composition further include a delaying component capable of delaying the reaction between the antiviral fusion protein and the aggregation-inducing component, or the coating composition is stored under conditions capable of delaying the reaction, as an example, under a low-temperature condition which is 0 to 15° C., as another example, 0 to 10° C.

Figure 3:
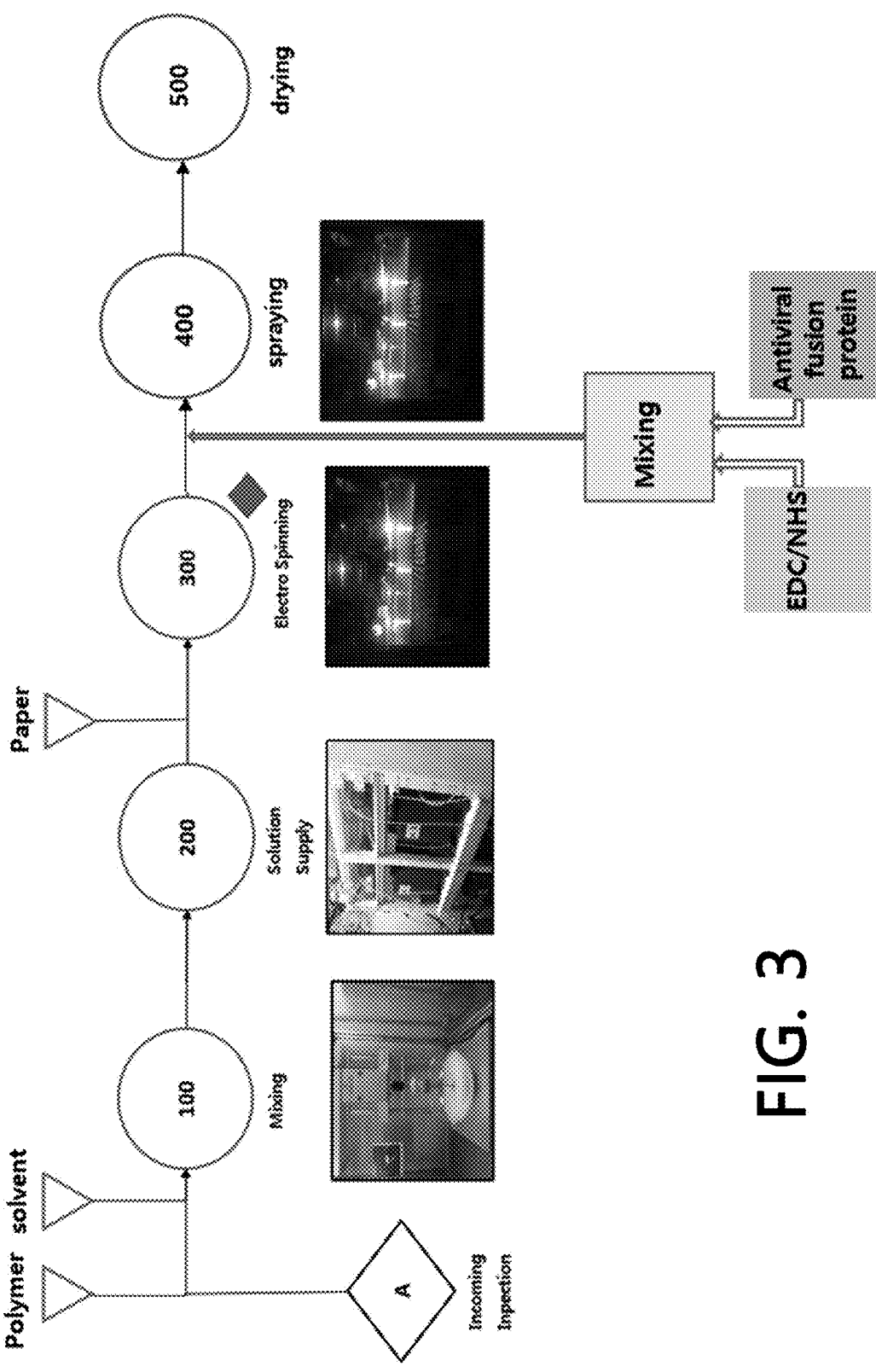
FIG. 3 is a process flow diagram for immobilizing an antiviral fusion protein on a nanofiber web according to one embodiment of the present invention, and specifically, is a view illustrating a process of mixing a spinning solution for preparing a nanofiber web 100, supplying an electrospinning device with the prepared spinning solution 200, preparing a nanofiber web through electrospinning 300, spraying an antiviral coating composition in which an antiviral fusion protein and EDC/NHS are mixed on the nanofiber web 400 and drying the sprayed antiviral coating composition 500.

Alternatively, as illustrated in FIG. 3, the antiviral coating composition is prepared using a first solution including an antiviral component and a second solution including an aggregation-inducing component, and then the first solution and the second solution are mixed according to the timing of treatment of the surface of the target, and then the surface of the target may be immediately treated with the mixture, or the surface of the target may be treated with the mixture after imparting a predetermined reaction time after mixing of the components.

When the process of preparing the coating composition containing the above-described aggregation-inducing component is looked at in detail, a second solution in which the aggregation-inducing component including the carbodiimide-based coupling agent and the reactive agent is dissolved in a solvent and a first solution in which the antiviral fusion protein is dissolved are each prepared, and then these solutions may be mixed at a predetermined content.

The first solution may be prepared by dissolving the prepared antiviral fusion protein in a solvent, for example, water.

In addition, the second solution may be prepared by mixing a carbodiimide-based coupling agent, a hydroxy succinimide-based reactive agent and a solvent, for example, water and/or ethanol, or prepared by preparing each of a mixed solution of a carbodiimide-based coupling agent and a solvent and a mixed solution of a hydroxy succinimide-based reactive agent and a solvent, and then mixing these mixed solutions.

In this case, the above-described active component may be included in the second solution, and for example, the second solution may be an activated solution obtained by mixing a carbodiimide-based coupling agent, a hydroxy succinimide-based reactive agent, and the active component, and then reacting the mixture for 1 to 60 minutes. Alternatively, the second solution may also be prepared by preparing each of a first mixed solution of a carbodiimide-based coupling agent and an active component and a second mixed solution of a hydroxy succinimide-based reactive agent and an active component, and then mixing these mixed solutions. In this case, two mixed solutions may be mixed with the first solution immediately after being mixed, but as another example, the two mixed solutions are mixed, and then the second solution may be prepared by inducing a reaction for 30 to 60 minutes.

Next, a step of mixing the prepared first and second solutions may be performed. In this case, the mixing ratio of the first solution and the second solution may be appropriately changed in consideration of a specific method of treating the surface with the antiviral coating composition, the thickness of a coating layer to be formed, the degree of antiviral activity, and the like. As an example, the first solution and the second solution may be mixed by adjusting the content, such that the total weight of the carbodiimide-based coupling agent and the hydroxy succinimide-based reactive agent is 50 to 200 parts by weight, as another example, 80 to 120 parts by weight, with respect to 100 parts by weight of the antiviral fusion protein. When the total weight of the carbodiimide-based coupling agent and the hydroxy succinimide-based reactive agent is less than 50 parts by weight, it may be difficult to implement a granular form, so that the coatability on the target surface may deteriorate. Furthermore, when the total content exceeds 200 parts by weight, the coating layer may be peeled off.

Meanwhile, after the mixing of the first solution and the second solution prepared as described above is performed, an aging step of inducing a reaction between the antiviral fusion protein in the first solution and the aggregation-inducing component in the second solution may be further performed.

Here, inducing a predetermined reaction means that the antiviral fusion protein is initiated to aggregate on the antiviral coating composition, or the surface of the target is treated in a state in which the antiviral fusion protein has already been aggregated to form particles having a predetermined size, and is not limited thereto, and it should be noted that an aggregation reaction may be induced by treating the surface of the substrate with the antiviral coating composition immediately after mixing the solutions. The aging step may be controlled by the content of the fusion protein and the aggregation-inducing component, the method of treating the target with the antiviral coating composition, and the like, and may be performed, as an example, for more than 0 to 300 minutes, and as another example, for 30 to 60 minutes. The aging time may also vary depending on the temperature conditions during aging, and the aging time during aging at low temperature may be increased. For example, when the surface of a substrate is coated with the antiviral coating composition using an impregnation method at room temperature, for example, 20 to 25° C., the aging time may be, as an example, 10 minutes or more, and as another example, 30 minutes, or 40 minutes or more. As another example, when the antiviral coating composition is electrosprayed, the aging time may be as an example, within 10 minutes, and as another example, within 8 minutes, 6 minutes, 4 minutes, and 2 minutes, for example, at 20 to 25° C.

In addition to the components described above, the above-described antiviral coating composition may further contain a component such as a dispersant, a leveling agent, a viscosity modifier, and an antifoaming agent, which are contained in a typical coating composition, and the specific types and contents thereof are not particularly limited in the present invention, because the known types may be used by adjusting the content to an appropriate content depending on the purpose.

Further, the antiviral fusion protein in the above-described antiviral coating composition may be immobilized on the surface of a desired target through the treating of the surface of the target with the antiviral coating composition and the drying of the antiviral coating composition.

The target may be an article or structure implemented with materials that may be brought into contact with humans, such as resin, paper, plastic, rubber, glass, metal, concrete, wood, paint, fiber, leather, and stone. Examples of the article include fibers, fabrics made of fibers, fabrics such as knitted fabrics or nonwoven fabrics and nanofiber web fabrics, air filters in which fabrics are used, water treatment filters, general clothing, special clothing for medical use, interior/building materials such as wallpaper, floors materials, and blinds, various types of wrapping paper, electrical and electronic parts or instruments such as outlet covers and various electric wires, furniture such as chairs and sofas, and the like. In addition, the structure may be, for example, a wall and floor of a building, and the like. Furthermore, the surface of the target may be rough or smooth, and flat or curved, and can be applied to surfaces with any shape and structure, which may have no pores or have pores.

Further, the surface of the desired target may be treated with the antiviral coating composition through a known coating method, and the known coating method may be, for example, impregnation, spin coating, comma coating, spraying, electrospraying, and the like. In addition, the antiviral coating composition may be implemented to have an appropriate viscosity according to a specific coating method.

When looking specifically at the case where the antiviral coating composition, particularly, the antiviral coating composition further including an aggregation-inducing component is applied onto the surface of the target by electrospraying, the electrospraying may be performed using a known electrospraying device. In this case, the conditions of the electrospraying are as follows: the distance between a tip and a collector may be 10 to 50 cm, the voltage applied to the tip may be 30 to 70 kV, the temperature during spraying may be 20 to 40° C., the relative humidity may be 30 to 50%, and through this, it may be suitable for implementing an antiviral coating layer which is uniform and exhibits the desired effect of the present invention.

Furthermore, when the target to be treated with the antiviral coating composition is a porous substrate such as a nonwoven fabric or a nanofiber web, only one surface of the nonwoven fabric or nanofiber web may be treated with the antiviral coating composition, or the position of a fiber forming the nonwoven fabric or nanofiber web, that is, the surface of the fiber located outside or inside may be treated with the antiviral coating composition, such that the surface of the fiber may be brought into contact with the antiviral coating composition. Further, the antiviral coating layer may be formed by appropriately adjusting the concentration of each component in the antiviral coating layer, the aging time, and the like such that the pores retained before treatment are not blocked even after the antiviral coating layer is formed.

In addition, after the surface of the target is treated with the antiviral coating composition, a reaction may be induced for a predetermined time such that the antiviral coating layer is formed. In this case, the reaction time may vary depending on the concentration of the antiviral fusion protein in the coating composition, the concentration of the aggregation-inducing component, the thickness of the desired coating layer, the time taken for the antiviral coating composition to react after penetrating into a target when the target is a porous substrate, the temperature, and the like.

Furthermore, the antiviral coating composition for which the reaction has been induced is then dried naturally at room temperature for 1 to 24 hours or dried with hot air and/or an IR lamp at a temperature of 30 to 100° C., so that the antiviral fusion protein may form particles on the surface of the target to implement an antiviral coating layer bound to the surface of the target.

Meanwhile, the above-described antiviral coating composition has been described as a coating application applied to the surface of an object, but is not limited thereto, and may be provided together with a desired object when the object is implemented, so that the object itself may incorporate the antiviral motif. As specific forms for this, it is possible to use various usage forms such as particles containing antiviral motif fusion proteins, paints containing antiviral motif fusion proteins, fibers containing antiviral motif fusion proteins, paper containing antiviral motif fusion proteins, plastics containing antiviral motif fusion proteins, films containing antiviral motif fusion proteins, and aerosols containing antiviral motif fusion proteins.

The following Table 1 shows the amino acid sequences for the antiviral motifs (SEQ ID NO: 1 to SEQ ID NO: 8) and adhesive proteins (SEQ ID NO: 9 to SEQ ID NO: 22) described above.

TABLE 1

| SEQ ID NO | Amino acid sequence |
|---|---|
| 1 | Lys Lys Lys Lys Tyr Arg Asn Ile Arg Arg Pro Gly |
| 2 | Thr Leu Lys Pro Ile Phe Lys Leu Pro Leu Gly Ile Asn Ile Thr Asn Phe Arg |
| 3 | Phe His Arg Lys Lys Gly Arg Gly Lys His Lys |
| 4 | Ser Leu Ile Gly Arg Leu |
| 5 | Trp Leu Val Phe Phe Val Ile Phe Tyr Phe Phe Arg Arg Arg Lys Lys |
| 6 | Arg Arg Lys Lys Trp Leu Val Phe Phe Val Ile Phe Tyr Phe Phe Arg |
| 7 | Arg Arg Lys Lys Ala Ala Val Ala Leu Leu Pro Ala Val Leu Leu Ala Leu Leu Ala Pro |
| 8 | Lys Leu Leu Leu Lys Leu Leu Lys Lys Leu Leu Lys Leu Leu Lys Lys Lys |
| 9 | Ala Lys Pro Ser Tyr Pro Pro Thr Tyr Lys |
| 10 | Ala Lys Pro Ser Tyr Pro Pro Thr Tyr Lys Ala Lys Pro Ser Tyr Pro Pro Thr Tyr Lys |
| 11 | Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys Ala Lys Pro Ser Tyr Pro Pro Thr Tyr Lys |
| 12 | Glu Val His Ala Cys Lys Pro Asn Pro Cys Lys Asn Asn Gly Arg Cys Tyr Pro Asp Gly Lys Thr Gly Tyr Lys Cys Lys Cys Val Gly Gly Tyr Ser Gly Pro Thr Cys Ala Cys |
| 13 | Ala Asp Tyr Tyr Gly Pro Lys Tyr Gly Pro Pro Arg Arg Tyr Gly Gly Gly Asn Tyr Asn Arg Tyr Gly Gly Ser Arg Arg Tyr Gly Gly Tyr Lys Gly Trp Asn Asn Gly Trp Lys Arg Gly Arg Trp Gly Arg Lys Tyr Tyr Glu Phe Glu Phe |
| 14 | Ala Asp Tyr Tyr Gly Pro Lys Tyr Gly Pro Pro Arg Arg Tyr Gly Gly Gly Asn Tyr Asn Arg Tyr Gly Arg Arg Tyr Gly Gly Tyr Lys Gly Trp Asn Asn Gly Trp Lys Arg Gly Arg Trp Gly Arg Lys Tyr Tyr |
| 15 | Gly His Val His Arg His Arg Val Leu His Lys His Val His Asn His Arg Val Leu His Lys His Leu His Lys His Gln Val Leu His Gly His Val His Arg His Gln Val Leu His Lys His Val His Asn His Arg Val Leu His Lys His Leu His Lys His Gln Val Leu His |
| 16 | Ser Ser Glu Glu Tyr Lys Gly Gly Tyr Tyr Pro Gly Asn Ala Tyr His Tyr His Ser Gly Gly Ser Tyr His Gly Ser Gly Tyr His Gly Gly Tyr Lys Gly Lys Tyr Tyr Gly Lys Ala Lys Lys Tyr Tyr Tyr Lys Tyr Lys Asn Ser Gly |

TABLE 1-continued

| SEQ ID NO | Amino acid sequence |
|---|---|
| | Lys Tyr Lys Tyr Leu Lys Lys Ala Arg Lys Tyr His Arg Lys Gly Tyr Lys<br>Lys Tyr Tyr Gly Gly Ser Ser |
| 17 | Ser Ser Glu Glu Tyr Lys Gly Gly Tyr Tyr Pro Gly Asn Thr Tyr His Tyr<br>His Ser Gly Gly Ser Tyr His Gly Ser Gly Tyr His Gly Gly Tyr Lys Gly<br>Lys Tyr Tyr Gly Lys Ala Lys Lys Tyr Tyr Tyr Lys Tyr Lys Asn Ser Gly<br>Lys Tyr Lys Tyr Leu Lys Lys Ala Arg Lys Tyr His Arg Lys Gly Tyr Lys<br>Lys Tyr Tyr Gly Gly Gly Ser Ser |
| 18 | Tyr Asp Asp Tyr Ser Asp Gly Tyr Tyr Pro Gly Ser Ala Tyr Asn Tyr Pro<br>Ser Gly Ser His Trp His Gly His Gly Tyr Lys Gly Lys Tyr Tyr Gly Lys<br>Gly Lys Lys Tyr Tyr Tyr Lys Phe Lys Arg Thr Gly Lys Tyr Lys Tyr Leu<br>Lys Lys Ala Arg Lys Tyr His Arg Lys Gly Tyr Lys Lys His Tyr Gly Gly<br>Ser Ser Ser |
| 19 | Ser Ser Glu Glu Tyr Lys Gly Gly Tyr Tyr Pro Gly Asn Thr Tyr His Tyr<br>His Ser Gly Gly Ser Tyr His Gly Ser Gly Tyr His Gly Gly Tyr Lys Gly<br>Lys Tyr Tyr Gly Lys Ala Lys Lys Tyr Tyr Tyr Lys Tyr Lys Asn Ser Gly<br>Lys Tyr Lys Tyr Leu Lys Lys Ala Arg Lys Tyr His Arg Lys Gly Tyr Lys<br>Lys Tyr Tyr Gly Gly Gly Ser Ser |
| 20 | Gly Gly Gly Asn Tyr Arg Gly Tyr Cys Ser Asn Lys Gly Cys Arg Ser Gly<br>Tyr Ile Phe Tyr Asp Asn Arg Gly Phe Cys Lys Tyr Gly Ser Ser Ser Tyr<br>Lys Tyr Asp Cys Gly Asn Tyr Ala Gly Cys Cys Leu Pro Arg Asn Pro<br>Tyr Gly Arg Val Lys Tyr Tyr Cys Thr Lys Lys Tyr Ser Cys Pro Asp Asp<br>Phe Tyr Tyr Tyr Asn Asn Lys Gly Tyr Tyr Tyr Asn Asp Lys Asp<br>Tyr Phe Asn Cys Gly Ser Tyr Asn Gly Cys Cys Leu Arg Ser Gly Tyr |
| 21 | Ala Lys Pro Ser Tyr Pro Pro Thr Tyr Lys Ala Lys Pro Ser Tyr Pro Pro<br>Thr Tyr Lys Ala Lys Pro Ser Tyr Pro Pro Thr Tyr Lys Ala Lys Pro Ser<br>Tyr Pro Pro Thr Tyr Lys Ala Lys Pro Ser Tyr Pro Pro Thr Tyr Lys Ala<br>Lys Pro Ser Tyr Pro Pro Thr Tyr Lys Ser Ser Glu Glu Tyr Lys Gly Gly<br>Tyr Tyr Pro Gly Asn Ala Tyr His Tyr His Ser Gly Gly Ser Tyr His Gly<br>Ser Gly Tyr His Gly Gly Tyr Lys Gly Lys Tyr Tyr Gly Lys Ala Lys Lys<br>Tyr Tyr Tyr Lys Tyr Lys Asn Ser Gly Lys Tyr Lys Tyr Leu Lys Lys Ala<br>Arg Lys Tyr His Arg Lys Gly Tyr Lys Tyr Tyr Gly Gly Ser Ser Ala Lys<br>Pro Ser Tyr Pro Pro Thr Tyr Lys Ala Lys Pro Ser Tyr Pro Pro Thr Tyr<br>Lys Ala Lys Pro Ser Tyr Pro Pro Thr Tyr Lys Ala Lys Pro Ser Tyr Pro<br>Pro Thr Tyr Lys Ala Lys Pro Ser Tyr Pro Pro Thr Tyr Lys Ala Lys Pro<br>Ser Tyr Pro Pro Thr Tyr Lys |
| 22 | Ala Lys Pro Ser Tyr Pro Pro Thr Tyr Lys Ala Lys Pro Ser Tyr Pro Pro<br>Thr Tyr Lys Ala Lys Pro Ser Tyr Pro Pro Thr Tyr Lys Ala Lys Pro Ser<br>Tyr Pro Pro Thr Tyr Lys Ala Lys Pro Ser Tyr Pro Pro Thr Tyr Lys Ala<br>Lys Pro Ser Tyr Pro Pro Thr Tyr Lys Ser Ser Glu Glu Tyr Lys Gly Gly<br>Tyr Tyr Pro Gly Asn Thr Tyr His Tyr His Ser Gly Gly Ser Tyr His Gly<br>Ser Gly Tyr His Gly Gly Tyr Lys Gly Lys Tyr Tyr Gly Lys Ala Lys Lys<br>Tyr Tyr Tyr Lys Tyr Lys Asn Ser Gly Lys Tyr Lys Tyr Leu Lys Lys Ala<br>Arg Lys Tyr His Arg Lys Gly Tyr Lys Lys Tyr Tyr Gly Gly Gly Ser Ser<br>Ala Lys Pro Ser Tyr Pro Pro Thr Tyr Lys Ala Lys Pro Ser Tyr Pro Pro<br>Thr Tyr Lys Ala Lys Pro Ser Tyr Pro Pro Thr Tyr Lys Ala Lys Pro Ser<br>Tyr Pro Pro Thr Tyr Lys Ala Lys Pro Ser Tyr Pro Pro Thr Tyr Lys Ala<br>Lys Pro Ser Tyr Pro Pro Thr Tyr Lys |

The present invention will be described in more detail through the following Examples, but the following Examples are not intended to limit the scope of the present invention and should be interpreted to help the understanding of the present invention.

Example 1

After a spinning solution including a fiber-forming component, which is PVDF, was electrospun onto one surface of a second member which is a nonwoven fabric (NamYang Nonwoven Fabric Co., Ltd., CCP30) formed of a core-sheath type composite fiber in which polyethylene with a thickness of about 20 μm and a melting point of about 120° C. serves as a sheath and polypropylene serves as a core, a target to be coated, which is a porous substrate in which a first member and a second member, which are PAN nanofiber webs, were fused was prepared by applying heat and a pressure of 1 kgf/cm² at a temperature of 140° C. by performing a calendering process.

After a first solution containing an antiviral fusion protein prepared through the following preparation example and water and a second solution in which a carbodiimide-based coupling agent and a hydroxy succinimide-based reactive agent were dissolved in ethanol were introduced into an electrospraying device through separate conduits without being mixed in the target to be coated, the device was designed such that the first solution and the second solution entered a spraying pack in the electrospraying device while being mixed through a Y-shaped conduit immediately before the spraying pack, and in this case, the first solution and the second solution were allowed to pass through the Y-shaped conduit, such that the concentration of the antiviral fusion protein in the mixed first solution and second solution was 0.1 mg/ml, and the weight ratio of the total weight of the carbodiimide-based coupling agent and the hydroxy succin-imide-based reactive agent and the antiviral fusion protein was 1:1. Thereafter, electrospraying was performed on the surface of the target to be coated at a discharge rate of 20 ml/min, a distance of 40 cm between the tip and the collector, at a temperature of 30° C., a relative humidity of 45 RH %, and a voltage of 50 kV applied to the tip.

Thereafter, the target was allowed to pass an IR lamp for initial drying, and then dried with hot air at 70° C. to implement an antiviral coating layer by forming particles of the antiviral fusion protein immobilized on the surface.*

Preparation Example—Preparation of Antiviral Coating Composition

As the antiviral fusion protein, an antiviral fusion protein was prepared in which the carboxyl group terminus of a mussel-derived adhesive protein which is SEQ ID NO: 21 and the amino terminus of the antiviral motif which is SEQ ID NO: 8 were bound. In this case, the antiviral fusion protein was prepared by a recombinant protein production method using *Escherichia coli*.

Specifically, the first solution was prepared by dissolving the antiviral fusion protein in water. Further, the second solution was prepared by including a carbodiimide-based coupling agent which is 1-[3-(dimethylamino)propyl]-3-eth-ylcarboimide hydrochloride (EDC), a reactive agent which is N-hydroxysulfosuccinimide (Sulfo-NHS), sodium acetate which is an active component, and water as a solvent, specifically, including EDC and Sulfo-NHS so as to have a weight ratio of 1:1, including sodium acetate such that the weight ratio of sodium acetate based on the total weight of EDC and Sulfo-NHS was 1:0.3, and then stirring the result-ing mixture. Thereafter, the first solution and second solu-tion prepared were stored at 20° C. and 5° C., respectively.

Example 2

An antiviral fusion protein was prepared in the same manner as in Example 1, and a surface, on which the antiviral fusion protein was immobilized, was prepared by introducing the following antiviral coating composition in which a tyrosine residue of an adhesive protein in the antiviral fusion protein was modified into a DOPA residue into an electrospraying device.

In this case, the modification into a DOPA residue was performed by dissolving the antiviral fusion protein in a buffer solution including 50 mM ascorbic acid to a concen-tration of 1 mg/ml, and in this case, as the buffer solution, a buffer solution of 40 mM sodium acetate and 20 mM sodium borate was used. Thereafter, the prepared solution was saturated with oxygen while injecting oxygen into the solution for 20 minutes, and then mushroom-derived tyro-sinase was added to a final concentration of 35 μg/ml. Thereafter, after mixing and stirring under oxygen condi-tions for 1 hour, acetic acid was added to a final concentra-tion of 5% to terminate the reaction after the modification reaction into a DOPA residue. Thereafter, the completed reaction solution was desalted and concentrated with a 5% acetic acid solution, and then subjected to a freeze-drying process to obtain an antiviral fusion protein containing a DOPA residue in a powder form. Thereafter, an antiviral coating composition was prepared by dissolving the obtained antiviral fusion protein to a concentration of 0.1 mg/ml using a 40 mM Tris buffer with a pH of 8.2.

Example 3

An antiviral fusion protein was prepared in the same manner as in Example 1, and a surface, on which the antiviral fusion protein was provided, was prepared using a solution of the antiviral fusion protein dissolved in water as an antiviral coating composition.

Comparative Example 1

An antiviral fusion protein was prepared in the same manner as in Example 1, and a surface, on which an antiviral motif was provided, was prepared by changing the antiviral fusion protein into the antiviral motif alone.

Experimental Example 1

The following physical properties were examined for the porous substrates having surfaces provided with the antiviral coating layer prepared in Examples 1 to 3 and Comparative Example 1, and the results are shown in the following Table 2.

1. Antiviral Performance

A target with a surface on which an antiviral coating layer was formed was prepared so as to have a width of 4 cm and a length of 4 cm. Thereafter, after each sample was treated with 200 ml of PED virus (coronaviridae, enveloped RNA virus) and then allowed to stand at 23° C. for 14 hours, the virus located on the sample was collected by adding 800 μl of an inoculation medium which is 1×DMEM (0.3% tryp-tose phosphate broth, 0.02% yeast extract, 1% antibiotic-antimycotic, 5 μg/ml trypsin) to the sample.

After an inoculation medium containing the collected virus was diluted by decimal dilution, 100 μl of the inocu-lation medium was inoculated into 5 wells per dilution factor, then adsorbed for 1 hour in a $CO_2$ incubator, then the inoculum was removed, and 200 μl of a virus culture medium per well was aliquoted to a 96-well plate containing VERO cells at $200 \times 10^4$ cells/well and incubated in an incubator for 5 days. Thereafter, the CPE of the cells was confirmed and the TCID value was calculated, and the resulting values are shown in the following Table 2.

The TCID log conversion value of the viral titer was 5.0000, a positive control was a result evaluated by allowing only 200 μl of the viral stock solution to stand at a tem-perature of 23° C. for 14 hours, and the TCID log conversion value was 5.0000.

2. Adhesion Performance

For Examples 1 to 3 which had antiviral performance among the porous substrates with an antiviral surface, impregnating each sample in water and then taking out the sample after 1 minute was defined as one set, and 20 sets were performed, and then the above antiviral performance was evaluated.

3. Storage Stability

After an accelerated aging test according to guidelines for setting the shelf life of medical devices and evaluating stability was performed by the following method, the stor-age stability of the porous substrate with an antiviral surface was evaluated by evaluating the above-described antiviral performance.

Specifically, in order to reproduce the real-time aging of the porous substrate within a shortened period of time, the porous substrate was prepared such that the aging period of each porous substrate was 3 year by storing the porous substrate at an elevated temperature (60° C.) for 3 months.

TABLE 2

|  | Example 1 | Example 2 | Example 3 | Comparative Example 1 |
|---|---|---|---|---|
| Immobilization target | Antiviral fusion protein | Antiviral fusion protein | Antiviral fusion protein | Antiviral motif |
| Additional immobilization method | EDC + Sulfo-NHS | Antiviral fusion protein DOPA modification | None | None |
| Antiviral performance (TCID log conversion value) | 3.5 | 3.8 | 4.6 | 5.0 |
| Adhesion performance (TCID log conversion value) | 3.5 | 3.9 | 5.0 | Not measured |
| Storage stability (TCID log conversion value) | 3.7 | 4.7 | 5.0 | Not measured |

As can be confirmed from Table 2, it can be seen that the antiviral performance of the surfaces having the antiviral coating layers formed according to Examples 1 and 2 is effectively present at 90% or more.

In addition, as a result of evaluating adhesion performance, there was little change in the antiviral performance of Examples 1 and 2, and in particular, there was no change in the antiviral performance according to Example 1, and through this, it can be seen that the method of immobilizing an antiviral fusion protein through Example 1 exhibits excellent adhesion characteristics on the surface.

Furthermore, as a result of the storage stability evaluation, Example 1 showed significantly less reduction in antiviral performance than the other Examples, and through this, it can be seen that storage stability is excellent.

Although one embodiment of the present invention has been described above, the spirit of the present invention is not limited to the embodiments presented in present specification, and a person skilled in the art who understands the spirit of the present invention can easily propose other embodiments by substitutions, changes, deletions, additions, and the like of the constituent elements, but it can be said that those embodiments also fall within the scope of the spirit of the present invention.

The invention claimed is:

1. A method for immobilizing an antiviral fusion protein on a surface, the method comprising:

preparing a first solution comprising an antiviral component and water, and a second solution comprising an aggregation-inducing component and ethanol, wherein the antiviral component comprises the antiviral fusion protein in which an antiviral motif is bound to the C-terminus or N-terminus of an adhesive protein, and wherein the aggregation-inducing component comprises a carbodiimide-based coupling agent and a hydroxy succinimide-based reactive agent;

mixing the first solution and the second solution in an electrospraying device to prepare an antiviral coating composition;

treating the surface with the antiviral coating composition through electrospraying; and drying the antiviral coating composition on the surface.

2. The method of claim 1, wherein a temperature of the second solution is 0 to 15° C.

3. The method of claim 1, further comprising: modifying a tyrosine residue possessed by the adhesive protein in the antiviral fusion protein into a DOPA residue before the treating of the surface with the antiviral coating composition.

4. The method of claim 3, wherein the modification comprises:

(1) preparing a solution in which the antiviral fusion protein is dissolved in a buffer solution containing ascorbic acid at a concentration of 25 to 100 mM such that the concentration is 0.1 to 10 mg/ml;

(2) preparing the solution in an oxygen-saturated state, and then modifying the tyrosine residue in the adhesive protein into the DOPA residue by mixing tyrosinase with the solution; and (3) performing desalting with acetic acid.

5. The method of claim 1, wherein the antiviral motif is a peptide selected from the group consisting of amino acid sequences of SEQ ID NOS: 1 to 8 or a peptide in which one or more of the amino acid sequences are linked.

6. The method of claim 1, wherein the adhesive protein is selected from the group consisting of amino acid sequences of SEQ ID NOS: 9 to 22 or a protein in which one or more of the amino acid sequences are linked.

7. The method of claim 1, wherein the adhesive protein is a mussel-derived adhesive protein.

8. The method of claim 1, wherein the antiviral coating composition further comprises sodium acetate as an active component that activates the aggregation-inducing component.

9. The method of claim 1, wherein the carbodiimide-based coupling agent and the hydroxy succinimide-based reactive agent are comprised in the aggregation-inducing component at a weight ratio of 1:0.5 to 20.

10. The method of claim 1, comprising mixing the carbodiimide-based coupling agent in an amount of 50 to 200 parts by weight with respect to 100 parts by weight of the antiviral fusion protein.

*     *     *     *     *

SEQUENCE LISTING

```
<160> NUMBER OF SEQ ID NOS: 22

<210> SEQ ID NO 1
<211> LENGTH: 12
<212> TYPE: PRT
<213> ORGANISM: Artificial Sequence
<220> FEATURE:
<223> OTHER INFORMATION: Antiviral peptide

<400> SEQUENCE: 1

Lys Lys Lys Lys Tyr Arg Asn Ile Arg Arg Pro Gly
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Antiviral peptide

<400> SEQUENCE: 2

Thr Leu Lys Pro Ile Phe Lys Leu Pro Leu Gly Ile Asn Ile Thr Asn
1               5                   10                  15

Phe Arg

<210> SEQ ID NO 3
<211> LENGTH: 10
<212> TYPE: PRT
<213> ORGANISM: Artificial Sequence
<220> FEATURE:
<223> OTHER INFORMATION: Antiviral peptide

<400> SEQUENCE: 3

Ala Lys Pro Ser Tyr Pro Pro Thr Tyr Lys
1               5                   10

<210> SEQ ID NO 4
<211> LENGTH: 6
<212> TYPE: PRT
<213> ORGANISM: Artificial Sequence
```

```
<220> FEATURE:
<223> OTHER INFORMATION: Antiviral peptide

<400> SEQUENCE: 4

Ser Leu Ile Gly Arg Leu
1               5

<210> SEQ ID NO 5
<211> LENGTH: 16
<212> TYPE: PRT
<213> ORGANISM: Artificial Sequence
<220> FEATURE:
<223> OTHER INFORMATION: Antiviral peptide

<400> SEQUENCE: 5

Trp Leu Val Phe Phe Val Ile Phe Tyr Phe Phe Arg Arg Arg Lys Lys
1               5                   10                  15

<210> SEQ ID NO 6
<211> LENGTH: 48
<212> TYPE: PRT
<213> ORGANISM: Artificial Sequence
<220> FEATURE:
<223> OTHER INFORMATION: Antiviral peptide

<400> SEQUENCE: 6

Ala Arg Gly Ala Arg Gly Leu Tyr Ser Leu Tyr Ser Thr Arg Pro Leu
1               5                   10                  15

Glu Ala Val Ala Leu Pro His Glu Pro His Glu Val Ala Leu Ile Leu
            20                  25                  30

Glu Pro His Glu Thr Tyr Arg Pro His Glu Pro His Glu Ala Arg Gly
        35                  40                  45

<210> SEQ ID NO 7
<211> LENGTH: 20
<212> TYPE: PRT
<213> ORGANISM: Artificial Sequence
<220> FEATURE:
<223> OTHER INFORMATION: Antiviral peptide

<400> SEQUENCE: 7

Arg Arg Lys Lys Ala Ala Val Ala Leu Leu Pro Ala Val Leu Leu Ala
1               5                   10                  15

Leu Leu Ala Pro
            20

<210> SEQ ID NO 8
<211> LENGTH: 17
<212> TYPE: PRT
<213> ORGANISM: Artificial Sequence
<220> FEATURE:
<223> OTHER INFORMATION: Anti-viral motif

<400> SEQUENCE: 8

Lys Leu Leu Leu Lys Leu Leu Lys Lys Leu Leu Lys Leu Leu Lys Lys
1               5                   10                  15

Lys

<210> SEQ ID NO 9
<211> LENGTH: 10
<212> TYPE: PRT
<213> ORGANISM: Artificial Sequence
<220> FEATURE:
<223> OTHER INFORMATION: adhesive protein
```

-continued

```
<400> SEQUENCE: 9

Ala Lys Pro Ser Tyr Pro Pro Thr Tyr Lys
1               5               10

<210> SEQ ID NO 10
<211> LENGTH: 20
<212> TYPE: PRT
<213> ORGANISM: Artificial Sequence
<220> FEATURE:
<223> OTHER INFORMATION: adhesive protein

<400> SEQUENCE: 10

Ala Lys Pro Ser Tyr Pro Pro Thr Tyr Lys Ala Lys Pro Ser Tyr Pro
1               5               10              15

Pro Thr Tyr Lys
            20

<210> SEQ ID NO 11
<211> LENGTH: 60
<212> TYPE: PRT
<213> ORGANISM: Artificial Sequence
<220> FEATURE:
<223> OTHER INFORMATION: adhesive protein

<400> SEQUENCE: 11

Ala Lys Pro Ser Tyr Pro Pro Thr Tyr Lys Ala Lys Pro Ser Tyr Pro
1               5               10              15

Pro Thr Tyr Lys Ala Lys Pro Ser Tyr Pro Pro Thr Tyr Lys Ala Lys
            20              25              30

Pro Ser Tyr Pro Pro Thr Tyr Lys Ala Lys Pro Ser Tyr Pro Pro Thr
        35              40              45

Tyr Lys Ala Lys Pro Ser Tyr Pro Pro Thr Tyr Lys
    50              55              60

<210> SEQ ID NO 12
<211> LENGTH: 39
<212> TYPE: PRT
<213> ORGANISM: Artificial Sequence
<220> FEATURE:
<223> OTHER INFORMATION: adhesive protein

<400> SEQUENCE: 12

Glu Val His Ala Cys Lys Pro Asn Pro Cys Lys Asn Asn Gly Arg Cys
1               5               10              15

Tyr Pro Asp Gly Lys Thr Gly Tyr Lys Cys Lys Cys Val Gly Gly Tyr
            20              25              30

Ser Gly Pro Thr Cys Ala Cys
        35

<210> SEQ ID NO 13
<211> LENGTH: 52
<212> TYPE: PRT
<213> ORGANISM: Artificial Sequence
<220> FEATURE:
<223> OTHER INFORMATION: adhesive protein

<400> SEQUENCE: 13

Ala Asp Tyr Tyr Gly Pro Lys Tyr Gly Pro Pro Arg Arg Tyr Gly Gly
1               5               10              15

Gly Asn Tyr Asn Arg Tyr Gly Gly Ser Arg Arg Tyr Gly Gly Tyr Lys
            20              25              30

Gly Trp Asn Asn Gly Trp Lys Arg Gly Arg Trp Gly Arg Lys Tyr Tyr
```

-continued

```
        35                40                45

Glu Phe Glu Phe
    50

<210> SEQ ID NO 14
<211> LENGTH: 46
<212> TYPE: PRT
<213> ORGANISM: Artificial Sequence
<220> FEATURE:
<223> OTHER INFORMATION: adhesive protein

<400> SEQUENCE: 14

Ala Asp Tyr Tyr Gly Pro Lys Tyr Gly Pro Pro Arg Arg Tyr Gly Gly
1               5                10                15

Gly Asn Tyr Asn Arg Tyr Gly Arg Arg Tyr Gly Gly Tyr Lys Gly Trp
            20                25                30

Asn Asn Gly Trp Lys Arg Gly Arg Trp Gly Arg Lys Tyr Tyr
        35                40                45

<210> SEQ ID NO 15
<211> LENGTH: 60
<212> TYPE: PRT
<213> ORGANISM: Artificial Sequence
<220> FEATURE:
<223> OTHER INFORMATION: adhesive protein

<400> SEQUENCE: 15

Gly His Val His Arg His Arg Val Leu His Lys His Val His Asn His
1               5                10                15

Arg Val Leu His Lys His Leu His Lys His Gln Val Leu His Gly His
            20                25                30

Val His Arg His Gln Val Leu His Lys His Val His Asn His Arg Val
        35                40                45

Leu His Lys His Leu His Lys His Gln Val Leu His
    50                55                60

<210> SEQ ID NO 16
<211> LENGTH: 75
<212> TYPE: PRT
<213> ORGANISM: Artificial Sequence
<220> FEATURE:
<223> OTHER INFORMATION: adhesive protein

<400> SEQUENCE: 16

Ser Ser Glu Glu Tyr Lys Gly Gly Tyr Tyr Pro Gly Asn Ala Tyr His
1               5                10                15

Tyr His Ser Gly Gly Ser Tyr His Gly Ser Gly Tyr His Gly Gly Tyr
            20                25                30

Lys Gly Lys Tyr Tyr Gly Lys Ala Lys Lys Tyr Tyr Tyr Lys Tyr Lys
        35                40                45

Asn Ser Gly Lys Tyr Lys Tyr Leu Lys Lys Ala Arg Lys Tyr His Arg
    50                55                60

Lys Gly Tyr Lys Lys Tyr Tyr Gly Gly Ser Ser
65                70                75

<210> SEQ ID NO 17
<211> LENGTH: 76
<212> TYPE: PRT
<213> ORGANISM: Artificial Sequence
<220> FEATURE:
<223> OTHER INFORMATION: adhesive protein
```

```
<400> SEQUENCE: 17

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser
65                  70                  75

<210> SEQ ID NO 18
<211> LENGTH: 71
<212> TYPE: PRT
<213> ORGANISM: Artificial Sequence
<220> FEATURE:
<223> OTHER INFORMATION: adhesive protein

<400> SEQUENCE: 18

Tyr Asp Asp Tyr Ser Asp Gly Tyr Tyr Pro Gly Ser Ala Tyr Asn Tyr
1               5                   10                  15

Pro Ser Gly Ser His Trp His Gly His Gly Tyr Lys Gly Lys Tyr Tyr
            20                  25                  30

Gly Lys Gly Lys Lys Tyr Tyr Tyr Lys Phe Lys Arg Thr Gly Lys Tyr
        35                  40                  45

Lys Tyr Leu Lys Lys Ala Arg Lys Tyr His Arg Lys Gly Tyr Lys Lys
    50                  55                  60

His Tyr Gly Gly Ser Ser Ser
65                  70

<210> SEQ ID NO 19
<211> LENGTH: 76
<212> TYPE: PRT
<213> ORGANISM: Artificial Sequence
<220> FEATURE:
<223> OTHER INFORMATION: adhesive protein

<400> SEQUENCE: 19

Ser Ser Glu Glu Tyr Lys Gly Gly Tyr Tyr Pro Gly Asn Thr Tyr His
1               5                   10                  15

Tyr His Ser Gly Gly Ser Tyr His Gly Ser Gly Tyr His Gly Gly Tyr
            20                  25                  30

Lys Gly Lys Tyr Tyr Gly Lys Ala Lys Lys Tyr Tyr Tyr Lys Tyr Lys
        35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser
65                  70                  75

<210> SEQ ID NO 20
<211> LENGTH: 99
<212> TYPE: PRT
<213> ORGANISM: Artificial Sequence
<220> FEATURE:
<223> OTHER INFORMATION: adhesive protein

<400> SEQUENCE: 20

Gly Gly Gly Asn Tyr Arg Gly Tyr Cys Ser Asn Lys Gly Cys Arg Ser
1               5                   10                  15
```

-continued

```
Gly Tyr Ile Phe Tyr Asp Asn Arg Gly Phe Cys Lys Tyr Gly Ser Ser
            20                  25                  30

Ser Tyr Lys Tyr Asp Cys Gly Asn Tyr Ala Gly Cys Cys Leu Pro Arg
            35                  40                  45

Asn Pro Tyr Gly Arg Val Lys Tyr Tyr Cys Thr Lys Lys Tyr Ser Cys
50                  55                  60

Pro Asp Asp Phe Tyr Tyr Tyr Asn Asn Lys Gly Tyr Tyr Tyr Tyr Asn
65                  70                  75                  80

Asp Lys Asp Tyr Phe Asn Cys Gly Ser Tyr Asn Gly Cys Cys Leu Arg
                    85                  90                  95

Ser Gly Tyr
```

```
<210> SEQ ID NO 21
<211> LENGTH: 194
<212> TYPE: PRT
<213> ORGANISM: Artificial Sequence
<220> FEATURE:
<223> OTHER INFORMATION: adhesive protein

<400> SEQUENCE: 21

Ala Lys Pro Ser Tyr Pro Pro Thr Tyr Lys Ala Lys Pro Ser Tyr Pro
1               5                   10                  15

Pro Thr Tyr Lys Ala Lys Pro Ser Tyr Pro Pro Thr Tyr Lys Ala Lys
            20                  25                  30

Pro Ser Tyr Pro Pro Thr Tyr Lys Ala Lys Pro Ser Tyr Pro Pro Thr
            35                  40                  45

Tyr Lys Ala Lys Pro Ser Tyr Pro Pro Thr Tyr Lys Ser Ser Glu Glu
    50                  55                  60

Tyr Lys Gly Gly Tyr Tyr Pro Gly Asn Ala Tyr His Tyr His Ser Gly
65                  70                  75                  80

Gly Ser Tyr His Gly Ser Gly Tyr His Gly Gly Tyr Lys Gly Lys Tyr
                85                  90                  95

Tyr Gly Lys Ala Lys Lys Tyr Tyr Tyr Lys Tyr Lys Asn Ser Gly Lys
            100                 105                 110

Tyr Lys Tyr Leu Lys Lys Ala Arg Lys Tyr His Arg Lys Gly Tyr Lys
            115                 120                 125

Tyr Tyr Gly Gly Ser Ser Ala Lys Pro Ser Tyr Pro Pro Thr Tyr Lys
    130                 135                 140

Ala Lys Pro Ser Tyr Pro Pro Thr Tyr Lys Ala Lys Pro Ser Tyr Pro
145                 150                 155                 160

Pro Thr Tyr Lys Ala Lys Pro Ser Tyr Pro Pro Thr Tyr Lys Ala Lys
            165                 170                 175

Pro Ser Tyr Pro Pro Thr Tyr Lys Ala Lys Pro Ser Tyr Pro Pro Thr
            180                 185                 190

Tyr Lys
```

```
<210> SEQ ID NO 22
<211> LENGTH: 194
<212> TYPE: PRT
<213> ORGANISM: Artificial Sequence
<220> FEATURE:
<223> OTHER INFORMATION: adhesive protein

<400> SEQUENCE: 22

Ala Lys Pro Ser Tyr Pro Pro Thr Tyr Lys Ala Lys Pro Ser Tyr Pro
1               5                   10                  15
```

-continued

```
Pro Thr Tyr Lys Ala Lys Pro Ser Tyr Pro Pro Thr Tyr Lys Ala Lys
            20              25              30

Pro Ser Tyr Pro Pro Thr Tyr Lys Ala Lys Pro Ser Tyr Pro Pro Thr
        35              40              45

Tyr Lys Ala Lys Pro Ser Tyr Pro Pro Thr Tyr Lys Ser Ser Glu Glu
    50              55              60

Tyr Lys Gly Gly Tyr Tyr Pro Gly Asn Ala Tyr His Tyr His Ser Gly
65              70              75                      80

Gly Ser Tyr His Gly Ser Gly Tyr His Gly Gly Tyr Lys Gly Lys Tyr
            85              90                      95

Tyr Gly Lys Ala Lys Lys Tyr Tyr Tyr Lys Tyr Lys Asn Ser Gly Lys
            100             105             110

Tyr Lys Tyr Leu Lys Lys Ala Arg Lys Tyr His Arg Lys Gly Tyr Lys
        115             120             125

Tyr Tyr Gly Gly Ser Ser Ala Lys Pro Ser Tyr Pro Pro Thr Tyr Lys
    130             135             140

Ala Lys Pro Ser Tyr Pro Pro Thr Tyr Lys Ala Lys Pro Ser Tyr Pro
145             150             155             160

Pro Thr Tyr Lys Ala Lys Pro Ser Tyr Pro Pro Thr Tyr Lys Ala Lys
            165             170             175

Pro Ser Tyr Pro Pro Thr Tyr Lys Ala Lys Pro Ser Tyr Pro Pro Thr
            180             185             190

Tyr Lys
```